United States Patent [19]

Sovak et al.

[11] Patent Number: 4,584,401
[45] Date of Patent: Apr. 22, 1986

[54] METHODS AND COMPOSITIONS INVOLVING POLYHYDROXYLATED POLYIODO NON-IONIC CONTRAST MEDIA

[75] Inventors: Milos Sovak, Rancho Santa Fe; Ramachandran Ranganathan, San Diego, both of Calif.

[73] Assignee: Biophysica Foundation, La Jolla, Calif.

[21] Appl. No.: 544,308

[22] Filed: Oct. 20, 1983

[51] Int. Cl.$^4$ .................. A61K 49/04; C07C 103/24; C07C 103/76
[52] U.S. Cl. .................................. 564/153; 564/156; 564/157; 564/167; 424/5
[58] Field of Search ............... 564/153, 156, 167, 157; 424/5

[56] References Cited

U.S. PATENT DOCUMENTS

| | | | |
|---|---|---|---|
| 3,701,771 | 10/1972 | Almen et al. | 424/5 X |
| 3,702,866 | 11/1972 | Salvesen et al. | 424/5 X |
| 3,953,501 | 4/1976 | Klieger et al. | 424/5 X |
| 4,001,323 | 1/1977 | Felder et al. | 424/5 X |
| 4,062,934 | 12/1977 | Tilly et al. | 424/5 |
| 4,250,113 | 2/1981 | Nordal et al. | 425/5 X |
| 4,341,756 | 7/1982 | Sovak et al. | 424/5 |
| 4,352,788 | 10/1982 | Felder et al. | 564/153 X |

FOREIGN PATENT DOCUMENTS

EP82803  6/1983  European Pat. Off. ............ 564/153

Primary Examiner—Thomas A. Waltz
Attorney, Agent, or Firm—Bertram I. Rowland

[57] ABSTRACT

Methods and compositions are provided for preparing polyhydroxylated polyiodo non-ionic contrast media. Particularly, substituted polyiodobenzamides are prepared, wherein the benzamide nitrogen is polyhydroxylated by allylic substitution on the nitrogen and oxidation of the olefinic group to provide for polyhydroxyl substitution. Amino substituents on the benzamide may be polyhydroxylated by allyl substitution or acryl substitution. All of the olefins may be oxidized simultaneously to glycols to provide for water soluble relatively non-toxic contrast media in efficient economical processes. Alternatively, the same compounds can be synthesized by alkylating N-acylbenzamide with polyacetoxyalkyl or dioxolanylalkyl halides, followed by removal of the protective groups.

6 Claims, No Drawings

METHODS AND COMPOSITIONS INVOLVING POLYHYDROXYLATED POLYIODO NON-IONIC CONTRAST MEDIA

BACKGROUND OF THE INVENTION

1. Field of the Invention

The development of non-ionic water-soluble contrast media illustrated that the toxicity of triiodinated benzene moieties can be decreased dramatically. It gave birth to a new generation of contrast media, which was very important, since ionic contrast media, despite their low cost have many undesirable side effects. Since the original development of Metrizamide ® efforts to develop better contrast media, both ionic and non-ionic, continued and have led to a second generation of compounds. Current ionic, monomeric contrast media are used to opacify the vascular or parenchymatic structures. With large doses of these media needed for contrast enhancement in computerized tomography and i.v. digital arteriography, the side effects become of great significance. Therefore, further improvements to decrease toxicity by developing economically feasible compounds are necessary and desirable.

In contra-distinction to the ionic contrast media materials, non-ionic contrast media have made a major contribution to the safety of the neuroradiology patient. In developing new non-ionic contrast media for vascular and urographic there is still ample room to achieve improvements as to many of the desired properties for a contrast medium. Important to an acceptable contrast medium is water solubility and low viscosity and the degree of biological inertness predicated by non-ionicity, high hydrophilicity and high iodine content and low osmolality. Since to a degree some of these properties are mutually exclusive, it is necessary to provide compromises in a final product.

In developing new products fulfilling the required properties, it is essential that processes be provided which allow for substantial flexibility in the groups attached to the aromatic ring. In addition, steps should provide for high yield, particularly in synthetic steps which appear late in the process. In addition, the materials employed should be relatively inexpensive, since contrast media are used in large amounts and, therefore, the cost of the contrast medium is a substantial factor of the cost of the diagnostic process.

2. Description of the Prior Art

U.S. Pat. No. 3,701,771, page 9, lines 70 ff, suggest substitution of the acylaminophenyl compound with allyl halide compounds to introduce a N-allylic group on the carbamoyl nitrogen, followed by permanganate oxidation to produce the dihydroxyalkyl group. U.S. Pat. No. 3,702,866 teaches the allylation of the polyiodinated acetanilide, followed by oxidation with manganese dioxide. The product is taught for use as a non-ionic contrast medium. Other patents of interest include U.S. Pat. Nos. 4,001,323, 4,021,481, 4,243,653, and 4,250,113. None of the prior art teaches use of benzamides.

SUMMARY OF THE INVENTION

Methods are provided for the efficient production of low-cost non-ionic polyiodo contrast media involving oxidation of poly(N-olefin N-polyacetoxyalkyl or N-dioxolanylalkyl substituted) triiodobenzamide to provide for a polyhydroxy derivative. Particularly, N-allyl polyiodobenzamide is employed which is further substituted with saturated or unsaturated acylated amino groups or allylated amido or amino groups to provide for a polyolefin substituted compound which is simultaneously polyhydroxylated by oxidation of the olefins. The olefinic intermediates provide precursors to non-ionic polyiodo contrast media.

DESCRIPTION OF THE SPECIFIC EMBODIMENTS

In accordance with the subject invention, polyhydroxylated non-ionic triiodobenzamide contrast media are provided where at least two olefinic, usually allylic substituents are present on different nitrogen atoms, which olefinic groups are simultaneously oxidized to introduce at least four and up to and including six hydroxyl groups. The triiodobenzamides will have from 1 to 3 carboxamide groups and from 0 to 2 annular amino groups, so as to have 3 substitutable nitrogen atoms (amino or amido). At least two of the nitrogen atoms are substituted with a 2-olefinic group, e.g., allyl or acryloyl.

For example, novel 2,4,6-triiodo-3,5-disubstituted benzamide derivates are prepared involving N-alkyl substituted benzamide, by substitution on an acylated benzamide nitrogen or reaction of a non-oxocarbonyl with allylamine. The 3- and 5-substituents may be amino which may be acylated or alkylated (saturated aliphatic) and allylated or acylated with acryloyl chloride; or may be carboxamide, where the amide nitrogen is acylated and allylated, or alkylated with protected hydroxyalkyl halides and the acyl group retained or removed. By providing for the introduction of a plurality of olefins, or protected hydroxyalkyl functions the nitrogens may be simultaneously inexpensively functionalized with hydroxyalkyl groups to provide for water solubility of the non-ionic contrast medium.

For the most part, the starting materials employed in the subject invention will have the following formula:

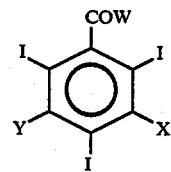

where X and Y are the same or different and are carboxy, actuated carboxy, carboxamide or amino, desirably X and Y being different; and W is hydroxy, amino or a group which activates the carbonyl to react with an amino to form a carboxamide.

Therefore, for the most part, the compounds of the subject invention will be diaminobenzamides, aminoisophthaldiamides, or trimesyltriamides or the acyl precursor. The starting compound is modified by substitution of at least one carboxamide group with an acyl group to provide an imide or reaction of at least one activated non-oxo-carbonyl with an allylamine. Usually, all the available nitrogen groups will be acylated, so that carboxamides will have imide nitrogens and amino groups will be amides. When the nitrogen atoms have been completely acylated, excess acyl groups can be removed to provide for alkylation sites. In addition to allylation, one or more nitrogen atoms may be alkylated with a saturated alkyl group of from 1 to 2 carbon atoms, e.g., methyl, or polyacetoxyalkyl groups or dioxolanylalkyl groups, from 2–4 carbon atoms.

Thus, the compounds are functionalized by acylation of the amide group and allylation or other alkylation of the resulting imide or reaction of an activated carbonyl, e.g., halide, anhydride or ester, with allylamine to provide the allylamide in one step. Depending upon the other functionalities, they may be treated in the same way or differently. Carboxy groups will be treated in the same way. Amino groups may be treated in a variety of ways. The amino group may be N-alkylated with alkyl halide of from 1 to 2 carbon atoms, particularly methylated, or with polyacetoxyalkyl or dioxolanylalkyl groups from 2–4 carbon atoms or acylated with acryloyl chloride; or may be acylated with a saturated aliphatic acid, e.g., an aliphatic acid of from 2 to 3 carbon atoms, followed by allylation.

The subject method permits the simultaneous introduction of olefinic functionalities at a plurality of sites employing the same olefinic reagent and, as required, a second step involving olefinic substitution of a remaining nitrogen, and also allows for the simultaneous oxidation of the olefins to glycols, so as to minimize the number of synthetic steps and enhance the efficiency of the synthesis.

Alternatively the subject method permits the simultaneous introduction of polyacetoxyalkyl or dioxolanylalkyl groups from 2–4 carbon atoms functionalities at a plurality of sites employing the same alkylating reagent followed by removal of the protecting groups.

The use of acryloyl chloride including alkyl or hydroxyalkyl derivatives of from 3 to 4 carbon atoms, e.g., acryloyl chloride derivatives such as protected 3-hydroxymethylacrylic chloride, etc., to provide for polyhydroxylated substituents has not been used previously in the preparation of non-ionic contrast media. The acryloyl chloride provides for amide formation which introduces a polar amide function as well as providing for an olefinic group which serves as a precursor to a glycol. Where an hydroxyl group is initially present, it will be protected by an acyl group e.g., acetyl, or an ether group, e.g., benzyl. Any protective group should be able to withstand the conditions employed for subsequent reactions and be readily removable, desirably being the same as other protective groups.

The use of acryloyl chloride is particularly advantageous in combination with allylic substituents, since the two olefinic groups may be simultaneously oxidized to glycols under the same mild conditions in good yield.

Also, acylation of available amino (includes amido) groups, particularly with acetic anhydride in the presence of a catalytic amount of a mineral acid is used imaginatively in the subject invention. Acylation of amide nitrogens provides for imides which can be allylated with allyl halides. Acylation of amino groups provides polar amides which may be retained or removed. Furthermore, polyacylated (including peracylated) amino groups may be readily hydrolyzed to remove one or two acyl groups to provide imido or amido nitrogen for further functionalization with aliphatic (alkyl or alkenyl) groups.

The polyunsaturated or hydroxylated intermediates will for the most part have the following formula:

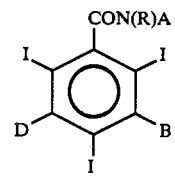

wherein:
B and D will be the same or different and will be of the formula:

CON(R)A or

N(V)UA' wherein:
A is of the formula:

—CH₂CH═CHT or

CH₂CH(OZ)CH(OZ)T where
T is hydrogen, methyl, or protected hydroxymethyl, particularly acylated, e.g., acetyl, or etherified, e.g., t.-butyl or benzyl;
R is hydrogen or alkyl of 1 to 2 carbon atoms, e.g., methyl;
V is hydrogen, methyl, or acetyl;
U is methylene or carbonyl (non-oxo-carbonyl);
A' is methyl or of the formula:

—CH═CHT or

CH(OZ)CH(OZ)T wherein:
T has been defined previously.

Upon oxidation, the olefins will become oxidized to glycols, so that A and A' will have the following formulae respectively:

CH₂CH(OZ)CH(OZ)T or

CH(OZ)CH(OZ)T wherein:
T has been defined previously and Z is hydrogen or a protective group, particularly acyl or two Zs may be taken together to form an acetal or ketal, wherein the Zs will be of from 1 to 4, usually 2 to 4 carbon atoms, and when taken together will be of 1 to 4, usually 2 to 4 carbon atoms. Particularly, Z will be acetyl, ethylidene or isopropylidene.

Preferably, at least one of B and D will have nitrogen bonded to an annular carbon atom. The preferred compounds will be where both B and D have nitrogen bonded to an annular carbon atom or one of B and D has a carbonyl bonded to an annular carbon atom. Thus, the preferred compounds will be the diaminobenzoic acid or aminoisophthalic acid.

Protective groups may be varied widely as a theoretical matter. However, as a practical matter, particularly because one of the roles of the subject process is the economical and efficient production of non-ionic contrast media, for the most part, the protective groups will be acetyl or isopropylidene.

Illustrative intermediate compounds include:
(2,4,6-triiodobenzamide will be abbreviated as TIB and 2,4,6-triiodoisophthaldiamide will be abbreviated as TII)
N-allyl 3,5-diacrylamido-TIB
N-(4'-acetoybut-2'-enyl-1') 3,5-diacrylamido-TIB
N,N'-diallyl,N,N'-diacetyl 5-(N''-methyl,N''-acetyl)-TII
N,N'-di(4'-acetoxybut-2'-enyl-1'), N''-methyl acetamido-TII
N,N',N''-triallyl 2,4,6-triiodotrimesyltriamide
N,N'-diallyl 5-acrylamido-TII
N-allyl 3,5-di(N'-methyl acrylamido) benzamide
N-acetyl-N-(2,3-dihydroxypropyl)-3,5-(N',N''-2,3-dihydroxypropyl)-acetylamino-TIB For the most part, the individual steps involved with the various synthetic sequences will employ conventional reagents and mild conditions. Acylation of nitrogen will involve either the acyl halide or acyl anhydride under mild conditions, generally at a temperature in the range of about −15° to 25° C. and in an inert dry polar solvent, such as N,N-dimethyl formamide or N,N-dimethyl acetamide. The concentrations may be wildly varied, depending upon the size of the reaction, the particular materials employed, and the like. Concentrations will generally vary from about 0.1 to 1M for the phenyl reactant (benzamide, benzoyl or aniline) and are either in stoichiometric amounts or slight excesses, usually not greater than about 25 mole percent excess of the phenyl compound will be employed.

The acylation of the amino or amido groups (-NH-) will preferably involve the use of the anhydride as an acetylating agent in the presence of a small amount (catalytic) of a strong mineral acid e.g., sulfuric acid, although the acyl halide particularly chloride, may also find use. Conveniently, the acyl anhydride may be used as the solvent, which will be used in significant excess, generally at least 5M excess, more usually at least about 10M excess. The mineral acid may be added slowly at reduced temperatures, followed by allowing the reaction to proceed over an extended period of time, generally at least about 6 hrs., at mild temperatures, generally from about 0° to 30° C.

The allyl amide may be achieved in two different ways, by use of allyl amine, which will normally involve the combination of an activated benzoyl, such as benzoyl halide e.g., chloride, and allylamine in the presence of a mild base e.g., carbonate. The reaction is carried out at reduced temperatures, generally below about 20° C., generally in the range of about −10° to +10° C. in an inert dry polar solvent e.g., an alkylated amide. The allylamine may be added to the acyl group in stoichiometric amounts or small excess, usually not more than about 1 mole excess.

An allylamide may also be achieved by acylation of an amide, followed by allylation of the resulting imide with an allyl halide, e.g., chloride. The allyl halide is added to the imide in an inert polar solvent e.g., DMSO, under mild conditions, generally, mildly elevated temperatures in the range of about 35° to 75° C. in the presence of a mild base e.g., carbonate. The allyl halide may be added to the imide and the reaction allowed to proceed to completion.

As an alternative to the allyl halide, an O-protected polyhydroxylated activated alkyl functions, such as halides, sulfonates, may be employed having an alkyl group of from 3 to 4 carbon atoms and from 2 to 3 protected oxy groups, esters and ethers, particularly acetoxy groups or acetals or ketals where the carbonyl compound is of from about 2 to 4 carbon atoms. Particularly the halide is α-chloro and the presence of the β-acyloxy group provides for an active halide which reacts with an imide or amino group in high yield.

Acyl groups may be readily removed from the allylated imide by treatment with an aqueous base, particularly an alkali metal hydroxide, at a predetermined pK. The reaction may be carried out at ambient temperatures, allowing the mixture to stand until the deacylation is complete. Deacylation can also be achieved in methanolic solution at room or lower temperature, in presence of trace amounts of sodium.

The oxidation of the olefins present in the polyolefin intermediate is carried out simultaneously, so that a polyglycol is produced in one step. Thus, from 4 to 6 hydroxyl groups are created simultaneously or substantially simultaneously. This provides for substantial advantages, since the yields can be quite high and a relatively inexpensive intermediate is modified to provide for the desired non-ionic contrast medium. Various conventional oxidants may be used, such as combinations of osmium tetroxide with a tert.-alkyl hydroperoxide, where the hydroperoxide is used substantially in excess of stoichiometric and the osmium tetroxide is used in catalytic amounts. The temperature for the reaction will generally be a mildly elevated temperature, generally in the range of about 35° to 75° C. Alternative oxidants include potassium permanganate, manganese dioxide, lead tetraacetate, and the like. Alternatively, epoxidizing agents may be employed or halohydrin agents may be employed to introduce the glycol. In both cases, the epoxide or halohydrin may be hydrolyzed, using acidic or basic catalysts, to provide for the glycol.

The products of the subject invention will for the most part have the following formula:

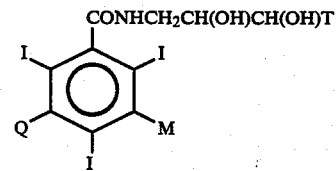

wherein:
T has been defined previously and
M and Q are the same or different and are of the formula:

wherein:
T has been defined previously;
d is 0 or 1;
R has been defined previously;

V is $H_2$ when d is 1 and oxygen when d is 0;

e is 0 or 1, with the proviso that T is hydrogen and V is $H_2$ when e is 0.

Illustrative compounds include:

N,N'-di(2', 3',4'-trihydroxybutyl) 5-(N"-methyl, 2",3",4"-trihydroxybutylamino)-TII N-(2',3'-dihydroxypropyl) 3,5-di(N'-methyl 2",3"-dihydroxypropylamino)-TIB N,N'-dimethyl, N,N'-di(2',3'-dihydroxypropyl) 5-(N"-methyl acetamido)-TII N,N'-di(2',3',4'-trihydroxybutyl) 5-(glyceramido)-TII N-(2',3'-dihydroxypropyl) 3,5-di(N'-methyl glyceramido)-TIB N,N',N"-(2',3'-dihydroxypropyl) 2,4,6-triiodotrimesyltriamide N,N'-di(2',3'-dihydroxypropyl) 5-(N"-methyl acetamido)-TII Purification of the final hydroxylated product can be achieved in a variety of ways, e.g., chromatography. A preferred way is to derivatize the available hydroxyl groups by O-acylation, e.g., O-acetylation, or ketal formation, e.g., acetonide, using acetone or acetone ketal, e.g., methyl or ethyl ketal. The product can usually be isolated in pure form by extraction from the aqueous medium with a substantially water immiscible solvent, e.g., chloroform, washing the organic layer and removing the solvent. The product may then be recrystallized from an hydroxylic solvent of low water solubility, e.g., higher alcohol. The O-substituents may be removed by acid hydrolysis, using, for example, an acid ion exchange resin in the crystallization solvent involving alcohol exchange.

The following examples are offered by way of illustration and not by way of limitation:

EXPERIMENTAL

EXAMPLE I

The preparation of N,N-di-(2',3'-dihydroxylpropyl) 5-(glycerylamido)-2,4,6-triodoisophthaldiamide.

The starting compound, 5-amino-2,4,6-triiodoisophthaloyl dichloride (I) was amidated with allylamine. The resulting isophthaldiamide (II) was acylated with acryloyl chloride, and this product (III) was oxidized to yield the final product (IV).

A. Amidation of 5-Amino-2,4,6-triiodoisophthaloyldichloride (I)

A solution of I (45.0 g. 76 mMoles) in 100 ml freshly distilled N,N-dimethyl acetamide was cooled to 5° C. on an ice bath, and potassium carbonate (21.0 g, 152 mMoles) was added. The heterogeneous mixture was allowed to cool for several minutes longer, after which time allylamine (13.8 g. 242 mMoles) was added over 10 minutes. After most of the heat of the reaction was dissipated, the ice bath was removed and the mixture was allowed to stir overnight at room temperature.

TLC (silica, 80 benzene/20 acetone) indicated that no starting material remained, and that a clean conversion to a single product had occurred.

The reaction was worked up by pouring it into an ice water slurry (1:1, 600 ml) accompanied by vigorous mechanical stirring. After the ice had melted, the precipitate was filtered off and washed to neutral pH with water (6×150 ml). The product was dried at 0.1 mm Hg and 40° C. over KOH pellets to yield N,N'-bis-allyl 5-amino-2,4,6-triiodoisophthaldiamide (II) as a white solid, 50.1 g (yield 98%).

B Acylation of N,N'-bis-allyl 5-amino-2,4,6-triiodoisophthaldiamide (II) with acryloyl chloride To an ice-cold solution of II (42.0 g, 66 mMoles) in 140 ml distilled N,N-dimethyl acetamide was added distilled acryloyl chloride (11.93 g, 132 mMoles) over a ten-minute period. The ice bath was removed, and the homogeneous solution was stirred at room temperature for an additional 16 hours. After this period, no starting material (II) could be seen by TLC (silica 95% $CHCl_3$/5% MeOH) and a fairly clean conversion to one slower-moving product was apparent.

The product was isolated by pouring the reaction mixture into ice water (1.5L), with mechanical stirring. The white solid was filtered on a fritted funnel, and washed well with water (4×200 ml). Drying at 0.1 mm Hg at 45° C. overnight afforded N,N'-bis-allyl 5-acrylamido 2,4,6-triiodoisophthaldiamide (III) as a granular white sold (45.0 g, 98%).

C. Oxidation of N,N'-bis-allyl 5-(acrylamido)-2,4,6-triiodoisophthaldiamide (III)

The following reagents were combined respectively to produce a heterogeneous mixture: N,N'-bis-allyl 5-acrylamido-2,4,6-triiodo isophthaldiamide (III, 5.0 g, 7.23 mMoles), tetrahydrofuran (25 ml. free of stabilizers), water (5 ml), t.-butyl hydroperoxide (70% solution, 5.63 g, 43.4 mMoles), tetraethylammonium acetate tetrahydrate (0.377 g, 1.45 mMoles) and osmium tetroxide (0.018 g, 0.0723 mMoles). The flask was then warmed to 50° C. on an oil bath for 20 hours.

TLC (silica, 60 chloroform/40 methanol) showed that no starting material (III) remained and demonstrated the presence of two products much more polar than III. (Rf 0.53 for a minor product and 0.30 for a major spot) Heating for an additional 60 hours at 50°–55° C. failed to alter the ratio of these two products.

The reaction mixture was cooled on an ice bath and sodium bisulfite (10% solution, 4.8 mMoles) was added to decompose excess oxidizing agents. The black heterogeneous mixture was evaporated to dryness on a rotary evaporator and the residue extracted with a 75 methanol/25 tetrahydrofuran mixture. The insoluble salts were filtered off and the solvent stripped from the filtrate to give a brown solid (4.85 g).

A small quantity of the brown solid (650 mg) was purified by preparative HPLC (Alltech 10 μM amino column; 1×25 cm; 90% acetonitrile/10% water) to give a very pure sample of the major product, N,N'-bis-(2,3-dihydroxypropyl) 5-glyceramido-2,4,6-triodo isophthaldiamide (IV).

EXAMPLE II

Preparation of a second non-ionic monomer was prepared by methylation of the isophthaldiamide (III) of Example I, followed by oxidation of the resulting product N,N'-bis-(2',3'-dihydroxypropyl) 5-(N"-methyl glyceramido)-2,4,6-triiodoisiophthaldiamide.

A. Methylation of N,N'-bis-allyl 5-(acrylamino isophthaldiamide (III)

The product N,N'-bis-allyl 5-(acrylamido-2,4,6-triiodoisophthaldiamide (III) was obtained in accordance with the procedure of Example I. This compound (III, 20.0 g, 29 mMoles) was added to distilled dimethyl sulfoxide (60 ml) and the mixture was warmed with a low-temperature heat gun to aid dissolution. The mixture was allowed to cool to room temperature, and potassium carbonate (6.0 g, 43 mMoles) was added as a solid. The heterogeneous mixture was cooled to 15° C. in an ice bath, and freshly distilled methyl iodide (7.38 g, 52 mMoles) was added neat over a ten-minute period. The reaction was allowed to run for 48 hours at room temperature, after which TLC (silica, 95% CHCl$_3$/5% MeOH) showed that all starting had been converted primarily to one faster-moving product.

The solution was poured into a stirred mixture of ice water (1:2, 500 ml) and the precipitated solid filtered off. The solid was washed well with water (4×200 ml) and dried in a funnel for 1 hour. Final drying was performed *in vacuo* (0.1 mm Hg) over NaOH pellets at 45° C. to give N,N'-bis-allyl 5-(N'-methyl acrylamido) 2,4,6-triiodoisophthaldiamide (V) as a white solid (19.0 g, 93%).

The product (18.0 g) was chromatographed on silica gel (480 g column, packed with CHCl$_3$), using a gradient from 0 to 5% methanol in chloroform (4L total). The yield of isolated product was 16.37 g, the compound being 97% purity by TLC. This compound was found to be identical with the same compound prepared by an alternate approach (conversion VIII–V described in Example 3).

B. Oxidation of N,N'-bis-allyl 5-(N"-methyl acrylamido) 2,4,6-triiodoisophthaldiamide (V)

In a 1L flask were combined N,N'-bis-allyl 5-(N"-methyl acrylamido) isophthaldiamide [(V) 50.0 g, 71 mMoles], acetone (400 ml), water (75 ml), potassium acetate (1.40 g, 14.2 mMoles, t.-butyl hydroperoxide (70%, 46.4 g, 355 mMoles) and osmium tetroxide (0.180 g, 0.71 mMoles, as a solution in 8.27 ml H$_2$O). The heterogeneous mixture was allowed to stir overnight at room temperature.

The reaction mixture was homogeneous, except for an oil which coated the flask walls; addition of 30 ml water led to a completely homogeneous system. TLC (silica, 60% n-butanol/30% water/10% HOAc) showed four products [Rf 0.48 (minor spot), 0.37 (major spot), 0.26 (major spot) and 0.19 (minor spot)], the two major spots making up at least 80% of the total UV-activity observed. HPLC (analytical, Merck "Li-Chrosorb II amino" column, 5 μM, 90% acetonitrile/10% 5N HOAC; flowrate 4 ml min$^{-1}$ gave peaks with retention times: 4.1 minutes, 5.5 minutes (very small peak), 6.7 minutes and 18.4 minutes (the latter by far the largest peak—at least 80%).

The reaction was allowed to proceed for an additional 60 hours (total reaction time=72 hours) at room temperature, at which time TLC showed virtual disappearance of the spot with Rf 0.48 and HPLC showed the same result for the peak with retention time 4.1 minutes (the peak at 6.7 minutes remained unaltered in intensity). Titration of an aliquot of the reaction mixture with a standard Na$_2$S$_2$O$_3$ solution indicated that slightly more than the theoretically required quantity of t.-butyl hydroperoxide has been consumed.

The reaction solution was diluted with 500 ml water, and was subsequently extracted with ethyl acetate (3×500 ml). Tests for t.-butyl hydroperoxide (KI-starch) and osmium (thiourea) indicated that both resided exclusively in the organic layer.

The aqueous layer was freed of small quantities of ethyl acetate by partial distillation on a rotary evaporator. The resulting aqueous solution was deionized on a Dowex 50 column (H+form, 554 cm$^3$, 62 eq H+/eq K+)and the water removed from the eluent to give 51.0 g of a white oily solid (90% yield after azeotroping with anhydrous ethyl alcohol, 3×50 ml).

The product (8.0 g) was purified by preparative HPLC (ANalytichem INternational "Sepralyte" (NH$_2$)), 40 μM; 2.5×50 cm; 85% acetonitrile/15% water) to yield 7.80 g of an off white foamy solid (98–99% purity). A small quantity (800 mg) of the product so purified was rechromatographed on a short prep column (Alltech 10 μM amino column, 1×25 cm. 85% acetonitrile/15% water) to give 570 mg of a pure sample.

Isolation of the two major product spots from prep TLC (i.e. those with Rf 0.37 and 0.26) and respotting on a fresh analytical plate again gave the same 2 spots in each case. Analytical HPLC employing the acetonitrile/water system (without HOAC) allowed resolution of the major product peak (i.e. that at 18.4 minutes in the acetonitrile/5N HOAC system) into 2 separate peaks. Collection of these two fractions separately followed by reinjections of each again gave two peaks in each case. These observations indicate that the two products are stereoisomers that interconvert under the isolation conditions. NMR's of the two major product spots were identical, corroborating the above conclusion.

EXAMPLE III

The isomer product of Example II was prepared by an alternate route utilizing a different starting compound. This procedure involved the amidation, and subsequent acylation, of 5-(N-methyl amino)-2,4,6-triiodoisophthaloyl dichloride (VII) to yield the product VI, converted to the isomer as described in Example II.

A. Amidation of 5-(N methyl-amino)-2,4,6-triiodisophthaloyl dichloride (VII)

A homogenous solution of (VII) (130.0 g, 213 mMoles), in 300 ml distilled N,N-dimethyl acetamide was cooled in ice bath to 5° C., and potassium carbonate (58.46, 426 mMoles) was added as a dry solid. Allylamine (36.5 g, 639 moles) was added neat over a forty minute period with an addition funnel. After all the amine had been added, the reaction mixture was allowed to warm to room temperature and was then stirred overnight. TLC (silica, 98% CHCl$_3$/2% MeOH) showed that no starting material (VII) remained, and that the product consisted almost exclusively of one spot.

Isolation of the product was accomplished by pouring the solution into a mechanically-stirred slurry of ice water (1:3, 2L). The product was filtered on a fritted funnel and was washed extensively with H$_2$O (3.5–4L). The white solid was dried at 0.5 mm Hg/50° C./over KOH pellets, then redried over P$_2$O$_5$/0.5 mm Hg/50° C./6 hours to obtain N,N'-bis-allyl 5-(N"-methyl amino)-2,4,6-triiodoisophthaldiamide (VIII, 129.07 g, 93%).

B. Acylation of N,N'-bis-allyl 5-(N"-methyl amino)2,4,6-triiodoisophthaldiamide (VIII)

In a 1L flask were combined N,N'-bis-allyl 5-(N-methyl-amino) 2,4,6-triiodoisophthaldiamide (VIII, 120 g, 184 mMoles) and freshly distilled N,N-dimethyl acetamide (350 ml). The homogenous golden-colored solution was cooled in an ice bath and freshly distilled acryloyl chloride (23.11 g, 255 mMoles) was added neat over ten minutes. The reaction was allowed to proceed overnight at room temperature under a drying tube. TLC (silica, 95% CHCl₃/5% MeOH) indicated that there had been almost exclusive conversion to a product slower-moving than the starting material (VIII), and that only a trace of starting material remained.

Workup was achieved by pouring the reaction solution into ice water (1:1, 2L), with vigorous mechanical stirring, followed by filtration of the precipitated solid. The white product was washed to neutral pH with water (5×400 ml) and then dried *in vacuo* (0.25 mm Hg) at 50° C. over NaOH pellets to obtain N,N'-bis-allyl 5-(N"-methyl acrylamido)-2,4,6-triiodoisophthaldiamide (V, 122.45 g, 98% yield).

The product was purified by recrystallization from tetrahydrofuran and methanol. Thus, 100 g crude solid gave 4 crops of white crystals, the total recovery being 77%. A fifth crop could be obtained (8%) but contained very significant quantities of impurities. TLC: (95 chloroform/5 methanol) Rf (VIII): 0.77; Rf (V): 0.62.

EXAMPLE IV

Another procedure for the preparation of the intermediate compound "V" was performed, which is then converted to the isomer as before. As in Example II, the starting material was the bis-chloride.

A. Amidation of 5-amino-2,4,6-triiodoisophthaloyldichloride (I) with ammonia A solution of 5-amino-2,4,6-triiodoisophthaloyl dichloride (I, 15.0 g, 25 mMoles) in 50 ml distilled N,N-dimethyl acetamide was placed in a 250 ml Parr pressure bomb and the contents cooled in an ice bath. A cold solution of anhydrous ammonia (ca 3.5 g, 206 mMoles) in N,N-dimethyl acetamide (20 ml) was quickly transferred to the bomb and the contents sealed. The reaction was allowed to proceed for 12 hours at 40° C., after which time the excess ammonia was vented and the bomb opened. TLC (silica, 80% CHCl₃/20% MeOH) indicated that no starting material (I) remained, and that one product was present.

The bomb was warmed at 55° C. for 1 hour to remove most of the ammonia, and the reaction mixture poured into a mechanically-stirred slurry of brine:ice:1.0N HCl (100 ml:100 g:25 ml). The product was filtered on a fritted funnel, washed with H₂O (3×50 ml), saturated aqueous sodium bicarbonate (25 ml) and finally H₂O (3×75 ml). The precipitate was dried overnight at 40° C. *in vacuo* over potassium hydroxide pellets to yield 5-amino-2,4,6-triiodoisophthaldi amide (IX). TLC: (80% CHCl₃/20% MeOH) Rf (IX): 0.51.

B. Acylation of 5-amino-2,4,6-triiodoisophthaldiamide (IX) with acryloyl chloride A heterogeneous suspension of 5-amino-2,4,6-triiodoisophthaldiamide (IX, 20.0 g, 36 mMoles) in freshly-distilled N,N-dimethyl acetamide (90 m) was cooled in an ice bath, and freshly distilled acryloyl chloride (6.5 g, 68 mMoles) was added over a three minute period. The ice bath was removed and the reaction allowed to proceed at room temperature for 48 hours. TLC (80% CHCl₃/20% MeOH) showed that the reaction was complete, no starting material (IX) remained and the product consisted almost exclusively of a single spot.

Workup was accomplished by pouring the reaction mixture into a slurry of ice water (1:3, 650 ml), with mechanical stirring. After the ice had melted, the precipitate was filtered off on a fritted funnel, and was washed to neutral pH with water (100 ml ×6). The produce was dried on the frit for 2 hours, and then *in vacuo* overnight at 0.1 mm Hg and 58° C. over potassium hydroxide pellets to give 5-acrylamido-2,4,6-triiodoisophthaldiamide (X) as a tan granular solid (19.20 g, 87.5% yield). THL: (80% CHCl₃/20% MeOH) Rf (IX): 0.51; Rf (X): 0.40.

C. Methylation of 5-acrylamido-2,4,6-triiodoisophthaldiamide (X) with methyl iodide A clear solution of 5-acrylamido-2,4,6-triiodoisophthaldiamide (X), (17.0 g, 28 mMoles) in freshly distilled dimethyl sulfoxide (125 ml) was mixed with potassium carbonate (5.8 g, 42 mMoles) and the heterogeneous mixture cooled to 15°-20° C. in an ice bath. Methyl iodide (7.95 g, 56 mMoles) was then added neat over a three-minute period, after which time the ice bath was removed and the reaction allowed to proceed at ambient temperature. TLC (80% CHCl₂/20% MeOH) after 24 hours showed that virtually no starting material (X) was left, and that conversion to one product had occurred.

The product was isolated by pouring the reaction mixture into 700 ml ice:brine (1:1). The precipitate was filtered off and was washed with water (5×50 ml). The white solid was dried overnight *in vacuo* at 60° C. and 0.3 mm Hg over potassium hydroxide pellets to give 5-(N-methyl acrylamido)-2,4,6-triiodoisophthaldiamide (XI). 15.7 g, 90% yield). TLC: (80% CHCl₃/20% MEOH):Rf (X):0.52; Rf (XI):0.63.

D. Acetylation of 5-(N-methyl)-2,4,6-triiodoisophthaldiamide (XI)

A heterogenous suspension of 5-(N-methyl acrylamido)-2,4,6-triiodoisophthaldiamide (XI, 6.25 g, 10 mMoles) in acetic anhydride (18 ml, 190 mMoles) was cooled in an ice bath, with magnetic stirring. Concentrated sulfuric acid (2 ml) was added dropwise over a three minute period, after which time the reaction was allowed to proceed overnight at room temperature. TLC (85 CHCl₃/15 MeOH) indicted that all starting material had been consumed and that one product was present corresponding to at least 90% of total UV-activity observed.

Workup was accomplished by pouring the solution into a vigorously-stirred slurry of ice/brine (1:1, 400 ml), followed by filtration of the precipitate. The white solid was washed with water to neutral pH (5×30 ml). Drying overnight at 25° C. and 0.3 mm Hg over potassium hydroxide pellets gave N,N'-bis-acetyl 5-(N"-methyl acrylamido)-2,4,6-triiodoisophthaldiamide (XII) as a granular solid (4.14 g, 58% yield). TLC: (85% CHCl₃/15% MeOH) Rf (XI): 0.54; Rf (XII): 0.70.

E. Allylation of N,N'-bis-acetyl 5-(N"-methyl acrylamido)-2,4,6-triiodoisophthaldiamide (XII)

N,N'-bis-acetyl 5-(N"-methyl acrylamido)-2,4,6-triiodoisophthaldiamide (XII, 2.13 g, 3 mMoles) was placed in a dry flask and freshly distilled dimethyl sulfoxide (6 ml) was added, with stirring. After a homogeneous solution was obtained, potassium carbonate (1.04 g, 7.5 mMoles) was added, followed by distilled allyl chloride (0.918 g, 12 mMoles) over a one minute period.

The reaction was allowed to proceed overnight at 45° C. under a condenser and a drying tube. TLC (90% CHCl₃/10% MeOH) showed that no starting material remained, and that 2 products were present: the major product (Rf=0.82, the desired di-allylated product) having an estimated 90% of the total UV-activity observed, and a minor component (Rf=0.70, the mono-allylated intermediate) having the bulk of the remaining UV activity.

The product was isolated by pouring the mixture into a stirred slurry of ice:brine:1.0N HCl (10 g:20 ml:10 ml) to give an orange granular precipitate. This solid was filtered off, washed with water to neutral pH (6×10 ml) and dried overnight at ambient temperature and 0.4 mm Hg over $P_2O_5$. This gave the expected product N,N'-bis-acetyl,N,N'-bis-allyl 5-(N''-methyl acrylamido)-2,4,6-triiodoisophthaldiamide (XIII, 2.05 g, 87% crude product yield).

The crude product (1.8 g) was chromatographed on silica gel, using a gradient of chloroform to 90% chloroform:10% acetone. Pooling of fractions and removal of the solvent gave 1.34 g of the purified product (XIII). TLC (90% $CHCl_3$:10% MeOH) Rf (XII):0.56; Rf (XIII):0.87.

F. Hydrolysis of N,N'-bis-allyl 5-(N''-methyl acrylamido)-2,4,6-triiodoisophthaldiamide (XIII)

A solution of 0.8 g N,N'-bis-acetyl-N,N'-bis-allyl 5-(N''-methyl acrylamido)-2,4,6-triiodoisophthaldiamide (XIII, 1.01 mMoles) in 5 ml dioxane and 5 ml 0.5N sodium hydroxide was heated at 40° C. for 2 hours on an oil bath. TLC (98% $CHCl_3$:2% MeOH) indicated that no starting material (XIII) remained, and that conversion to a single product had occurred.

The product was isolated by pouring the reaction mixture into an ice-brine slurry (1:1, 20 ml), followed by filtration of the resultant white precipitate. The solid was washed with water (6×5 ml), and then dried at 4 mm Hg and 62° C. for 60 hours to give N,N'-bis-allyl 5-(N''-methyl acrylamido)-2,4,6,-triiodoisophthaldiamide (V, 655 mg, 92% yield).

This compound was identical by TLC, NMR and IR to the same compound prepared previously by the two previously described routes (conversions III to V in Example II and VIII to V in Example III). TLC (98% $CHCl_3$/2% MeOH) Rf (XIII):0.59; Rf (V):0.26.

EXAMPLE V

The synthesis of N,N'-bis-(2',3'-dihydroxypropyl) 5-(N''-methyl acetamido)-2,4,6-triiodoisophthaldiamide (IX) was performed by alternate procedures.

1. Preparation from 5-(N-methyl amino)-2,4,6-triiodoisophthaloyl dichloride (VII).

A. Acetylation of 5-(N-methyl amino)-2,4,6-triiodoisophthaloyl dichloride (VII)

A homogenous solution of 5-(N-methyl amino)-2,4,6-triiodoisophthaloyl dichloride (VII, 61.0 g, 100 mMoles) in freshly-distilled N,N-dimethyl acetamide (125 ml) was cooled in an ice bath to 5°–10° C. and distilled acetyl chloride (11.78 g, 150 mMoles) was added over a three minute period.

The solution was warmed at 45° C. for four hours, after which time TLC (85% $CCl_4$/15% acetone) indicated that no starting material (VII) remained and that primarily one product was formed (approximately 95% of total UV activity observed).

The reaction mixture (now a heterogeneous paste) was poured into a mechanically-stirred slurry of ice water (1:1, 1L), the precipitate filtered and bashed with water (2×100 ml), saturated aqueous sodium bicarbonate (4×200 ml) and finally water to neutral pH (4×300 ml). The product was dried overnight at 40° C. and 0.3 mm Hg over KOH pellet, then redried over $P_2O_5$ to yield 5-(N-methyl acetamido)-2,4,6-triiodoisophthaloyl dichloride (XIV) as a slightly off-white, granular solid (60.0 g, 92% yield). TLC (85% $CCl_4$/15% acetone): Rf (XII):0.79; Rf (XIV):0.59.

B. Amidation of 5-(N-methyl acetamido)-2,4,6-triiodoisophthaloyl dichloride (XIV) with ammonia A solution of 5-(N-methyl acetamido)-2,4,6-triiodoisophthaloyl dichloride (XIV, 10.0 g, 15 mMoles) in 35 ml N,N-dimethyl acetamide was placed in a 250 ml Parr bomb and was cooled in an ice bath. Anhydrous ammonia (ca 2.55 g, 150 mMoles) in cold N,N-dimethyl acetamide (15 ml) was added to the bomb and the contents quickly sealed.

The mixture was heated at 45° C. for 8 hours and the excess ammonia vented prior to removing the cap. The open bomb was warmed at 50° C. for two hours to remove the bulk of the ammonia, and the contents dumped into a vigorously stirred slurry of ice, brine and 1.0N HCl (75 g:75 ml:30 ml). The precipitate was filtered off and washed with water until the filtrate was neutral (4×50 ml). The product was dried overnight at 0.5 mm Hg and 60° C. over KOH pellets to give 8.06 g. 5-(N-methyl acetamido)-2,4,6-triiodoisophthaldiamide (XV, 86% yield. TLC: (80% $CHCl_3$/20% MeOH) Rf (XV):0.52.

C. Acetylation of 5-(N-methyl acetamido)-2,4,6-triiodoisophthaldiamide (XV)

A heterogenous suspension of 5-(N-methyl acetamido)-2,4,6-triiodoisophthaldiamide (XV, 2.0 g, 3.3 mMoles) in acetic anhydride (6.3 ml) was stirred at room temperature, and concentrated sulfuric acid (0.66 ml) was added without cooling. A slight temperature rise (ca 5° C.) was noted after the addition of the acid, and the reaction mixture became nearly homogeneous with 15 minutes.

The reaction was allowed to proceed for three hours, at which time TLC (90% $CHCl_3$:10% MeOH) indicated at least a 95% conversion to a faster-moving product.

Workup was accomplished by pouring the solution into ice water (1:1, 50 ml). The resultant heterogenous slurry was stirred for an additional 20 minutes, and the precipitate filtered off. The product was washed with diluted brine (4×10 ml), saturated aqueous sodium bicarbonate (3×1 ml) and then water (3×2 ml). The white solid was dried overnight at 0.1 mm Hg and 55° C. over KOH pellets to give N,N'-bis-acetyl 5-(N''-methyl acetamido)-2,4,6-triiodoisophthaldiamide, 2.24 g, 98% yield). TLC (90% $CHCl_3$/10% MeOH) Rf (XV):0.26; Rf (XVI):0.51.

D. Alkylation and Hydrolysis of N,N'-bis-acetyl 5-(N''-methyl acetamido)-2,4,6-triiodoisophthaldiamide (XVI)

A solution of N,N'-bis-acetyl 5-(N''-methyl acetamido)-2,4,6-triiodoisophthaldiamide (XVI), 1.0 g, 1.43 mMoles) in dimethyl sulfoxide (8 ml) was mixed with potassium carbonate (1.0 g, 7.2 mMoles) and was warmed to 50° C. on an oil bath. Allyl chloride (0.671 g, 7.2 mMoles) was added over 5 minutes as a solution in 2 ml dimethyl sulfoxide. The reaction was allowed to proceed overnight at 50° C.

TLC (90% CHCl₃/10% MeOH) indicated that no starting material (XVI) remained, and that 2 products were present, the faster-moving of the 2 accounting for at least 90% of the UV-activity observed.

The products were hydrolyzed by addition of 2 ml 1.0N NaOH directly to the reaction mixture. TLC indicated that hydrolysis was complete within one hour.

The dark reddish solution was poured into a stirred mixture of ice and brine (2:1, 150 ml). After the ice melted, the heterogeneous aqueous layer was extracted with tetrahydrofuran (3×75 ml), and the combined tetrahydrofuran extracts were washed with 50% saturated brine (2×30 ml). The organic layer was dried over magnesium sulfate, the drying agent filtered off, and the solvent removed on a rotary evaporator to give 0.9 g of a crude brown solid. The products were chromatographed on silica gel, using a gradient of dichloromethane to dichloromethane:methanol (90:10). Pooling the appropriate fractions and removing the solvents on a rotary evaporator gave a yellow solid, N,N'-bis-allyl 5-(N''-methyl acetamido)-2,4,6-triiodoisophthaldiamide (XVIII, 0.675 g, 68% yield).

This product (XVIII) was identical by TLC. ¹H NMR and IR to the same compound prepared by an alternate route (conversion XIV→XVIII). TLC (90% CHCl₃/10% MeOH): Rf (XVI):0.51; Rf (XVII)0.89 Rf (XVIII):0.70.

E. Oxidation of N,N'-bis-allyl 5-(N''-methyl acetamido)-2,4,6-triiodoisophthaldiamide (XVIII)

A heterogeneous solution of N,N'-bis-allyl 5-(N''-methyl acetamido)-2,4,6-triiodoisophthaldiamide (XVIII, 2.5 g, 3.5 mMoles), acetone (20 ml), t.-butyl hydroperoxide (70% solution, 2.0 ml, 14.4 mMoles) tetraethylammonium acetate tetrahydrate (0.188 g, .0.72 mMoles) and osmium tetroxide (0.009 g, 0.36 mMoles) was prepared and heated to 55° C. on an oil bath. The solution soon became homogeneous and was allowed to run overnight at 50° C.

TLC (75% CHCl₃/25% MeOH) indicated that no starting material (XVIII) remained, and that 2 products were present, the slower moving of which made up approximately 85% of the total. Titrimetry with sodium thiosulfate showed that nearly the theoretically required quantity of t.-butyl hydroperoxide had been consumed.

The excess oxidizing agent was destroyed with 5% sodium bisulfite solution, with cooling, and the resultant black heterogeneous mixture distilled on a rotary evaporator to remove the acetone. The residue was dried by coevaporation with anhydrous ethanol (3×10 ml), the solid extracted with methanol and the insoluble black solids removed by filtration through celite. The solvent was removed to give a tan foamy solid.

This product was chromatographed on silica gel, using a gradient from 90% CHCl₃:10% MeOH to 50% CHCl₃:50% MeOH. The solvent was removed from the appropriate pooled fractions to give N,N'-2,3,-dihydroxypropyl 5-(N''-methyl acetamido)-2,4,6-triiodoisophthaldiamide (XIX, 1.65 g, 60% yield). This compound was identical by TLC, NMR and IR to the same compound prepared by an alternate route (conversion XIV→XIX). TLC (75% CHCl₃:25% MeOH): Rf (XIX):0.47.

2. Preparation from 5-(N-methyl acetamido) 2,4,6-triiodoisophthaloyl dichloride (XIV)

A. Amidation of 5-(N-methyl acetamido)-2,4,6-triiodoisophthaloyl dichloride (XIV) with Allylamine A heterogeneous suspension of 5-(N-methyl acetamido)-2,4,6-triiodoisophthaloyl dichloride (XIV, 8.0 g, 12.3 mMoles) in tetrahydrofuran (35 ml) was cooled to 5° C. on an ice bath, and allylamine (5.59 g, 97.9 mMoles) was added over 2 minutes. After the exothermic reaction had subsided, the now homogeneous solution was allowed to stir for one hour at room temperature.

No starting material (XIV) remained at this point by TLC (70% benzene: 30% acetone), and the product was predominately one spot.

The solvent was removed on a rotary evaporator and the solid residue suspended in a mixture of 1.0N HCl and brine (1:2, 30 ml). The insoluble white solid was filtered on a fritted funnel, washed with water (3×20 ml), saturated aqueous sodium bicarbonate (5 ml) and finally water (3×20 ml). The product was dried overnight at 60° C. and 3 mm Hg over potassium hydroxide pellets to give N,N'-bis-allyl 5-(N''-methyl acetamido)-2,4,6-triiodoisophthaldiamide (7.7 g, 91% yield). TLC (70% benzene:30% acetone) Rf (XIV):0.85; Rf (XVIII:0.44).

EXAMPLE V

Preparation of N,N',N''-tri-(2,3-dihydroxypropyl) 3,5-(bis-diacetamido)-2,4,6-triiodobenzamide from 3,5-diaminobenzamide (XX).

A. 3,5-Diaminobenzamide bis-Hydrochloride (XX)

3,5-Dinitrobenzamide (XIX) (85.0 g, 402 mMoles, Aldrich) was added to a suspension of 10% Pd/C (8.5 g) in concentrated HCl (74 ml) and water (730 ml). The mixture was hydrogenated at about 60 psi in a Parr hydrogenation apparatus until hydrogen was no longer being consumed (3 hours). TLC (silica, 80 chloroform/20 methanol) indicated that no starting material remained, and that to a single product with an Rf of 0.23 had occurred. The solution, which contained the product (XIX), was then filtered through a celite pack, the pack was washed with 300 ml water, and the filtrate and washings combined and used for the subsequent iodination.

B. 3,5-Diamino-2,4,6-triiodobenzamide (XXI)

The 3,5-diaminobenzamide bis-hydrochloride (XIX) in acid solution A was further diluted to 4.8L. This was stirred vigorously, and, over a twenty minute period, 3.2 equivalents of KICl₂ (80 ml of 2.08M KICl₂, 192 ml of 2.70M KICl₂ and 207 ml of 2.93M KICl₂) was added, resulting almost immediately in the precipitation of a brown solid. Fifteen minutes after all of the KICl₂ had been added, TLC (silica, 85 chloroform/15 methanol) indicated that no starting material remained, and that conversion to a single product with an Rf of 0.63 had occurred.

The brown solid was filtered and washed with 1L of water. To remove traces of KICl₂ or ICl, the solid was suspended in 300 ml 5% NaHSO₃, filtered, and washed with 300 ml 0.1N HCl followed by 400 ml water. The product was dried *in vacuo* to yield 3,5-diamino-2,4,6-triiodobenzamide (XXI) as a brown solid, 164 g (77% based on I).

C. Acetylation of 3,5-Diamino-2,4,6-triiodobenzamide-(XXI)

Concentrated sulfuric acid (28 ml) was added with vigorous stirring to an ice-cooled, brown slurry of 3,5-diamino-2,4,6-triiodobenzamide (XXI) (150.0 g, 284 mMole) in acetic anhydride (567 ml). The ice bath was removed and, after two hours, a tarry, brown soid formed and the stirring terminated. An additional 250 ml of acetic anhydride and 12.5 ml of concentrated sulfuric acid was added, which led to complete dissolution of the tarry solid over a 15 minute period, to yield a deep brown homogeneous solution. A tan precipitate formed. After 10.5 hours, TLC (silica, 90 chloroform/10 ethanol) indicated that the reaction had yielded a mixture of four products, two of which accounted for more than 95% of the mixture.

Workup consisted of slowly pouring the reaction mixture into four times its volume of water. The precipitate was then filtered, washed with 800 ml cold water and dried *in vacuo* to yield a tan colored product (136.3 g, 66% crude yield).

The crude product was recrystallized from acetone/hexane in the following manner: 103 g was dissolved in 800 ml hot acetone to yield a murky, violet colored solution. The solution was treated with 2 g decolorizing charcoal and filtered through a celite pack, to yield a deep yellow, clear solution. A second treatment with 2 g decolorizing charcoal did not lead to a lighter colored solution. The solution was concentrated to about 400 ml on a hot plate, and then hexanes (about 300 ml) were added to cause slight turbidity. White crystals formed quickly in small circular patches, which adhered tightly to the glass walls of the flask. The crystals were dislodged from the glass, filtered, washed with a 2:1 mixture of acetone and hexane, and dried. Three additional crops were obtained to yield N-acetyl 3,5-bis-(diacetylamido)-2,4,6-triiodobenzamide (XXII) as a white microcrystalline solid (82.8 g, 53% yield from XXI).

TLC on silica with 90 chloroform/10 ethanol showed that the crude product consisted of a mixture of four components present in the ratio of 17:1:80:2 having Rf's of 0.56, 0.61, 0.66 and 0.72, respectively. Recrystallized material (XXII) provided a mixture consisting of three components in the ratio of 2:1:97 having Rf's of 0.56, 0.61 and 0.66, respectively. HPLC showed that the recrystallized material (XXII) was greater than 98% pure with a retention time of 3.5 minutes. Column: Merck LiChrosorb CN (5 μm). Solvent system: 85 cyclohexane/9 tetrahydrofuran/3 methanol/3 isobutanol. Flow rate: 2 ml/min.

D. N,N',N''-triallyl 3,5-bis-(acetamido)-2,4,6-triiodobenzamide (XXIII)

N-Acetyl 3,5-bis-(diacetylamido)-2,4,6-triiodobenzamide (XXII) (36.94 g, 150.0 mMoles) was dissolved in dimethyl sulfoxide (150 ml, distilled from CaH$_2$) in a dry flask fitted with a mechanical stirrer to yield a clear yellow, homogeneous solution. Potassium hydroxide (15.30 g, 273 mMole, powdered and dried *in vacuo* at 65° C.) was added over a 2¼ hour period in ten approximately equal portions. During the addition the yellow color deepened, much of the KOH did not appear to dissolve, and other white solids precipitated from solution. By TLC (silica, 90 chloroform/10 ethanol) the reaction appeared to have gone to roughly 50% completion and then stopped soon after the addition of KOH. Additional KOH (2.10 g, 37.5 mMole) was added. The following morning deacetylation was observed to have yielded a mixture consisting of five components; two of these which accounted for approximately 95% of the mixture, were in a 95:5 ratio, and had Rf's of 0.21 and 0.08 respectively.

To allylate the triacetyl compound (XXIV), potassium bicarbonate (13.8 g, 100 mMole, dried *in vacuo* at 65° C.), and allyl chloride (24.5 ml, 300 mMole, freshly distilled at 45°-46° C.) were added, in this sequence, while cooling the flask in an ice bath. The ice bath was removed, the color of the reaction mixture slowly darkened to a deep brown, and more solid material precipitated. Allylation to XXV was complete within 23 hours. Methanol (100 ml) was added and within 15 minutes deacetylation to a mixture containing greater than 90% (XXIII) had occurred. XXIII split into three isomeric components by TLC with Rf's of 0.58, 0.59 and 0.62.

Workup consisted of pouring the reaction mixture very slowly into a stirred, ice-cooled solution of 1N HCl (450 ml) and brine (1800 ml). The resulting precipitate was filtered, washed with water (700 ml) and dried *in vacuo* to yield a brown solid (31.6 g, 86% crude yield).

The N,N',N''-triallyl 3,5-bis-acetamido-2,4,6-triiodobenzamide was purified by filtration through silica gel followed by recrystallization from aqueous methanol. The crude product (39.35 g) was dissolved in dichloromethane (200 ml) and then filtered through silica gel (200 g, 40-140 mesh). The silica gel was washed successively with CH$_2$Cl$_2$ (600 ml), 1% methanol in CH$_2$Cl$_2$ (500 ml), 2% methanol in CH$_2$Cl$_2$ (500 ml) and 3% methanol in CH$_2$Cl$_2$ (1750 ml). The filtrate and washes were combined and the solvents removed to yield a brown solid (38.00 g). This was dissolved in methanol (400 ml) to yield a brown solution. The solution was treated with 3.8 g decolorizing charcoal and filtered through a celite pack to yield a deep yellow solution. A second treatment with charcoal did not lead to a lighter colored solution. The solution was concentrated to 150 ml and water (ca 60 ml) was added until a few small, needle-like crystals formed. The solution was allowed to cool slowly at room temperature, and the resulting pale yellow crystals of VII were collected and washed with 2:1 mixture of methanol and water. TLC, on silica with 90 chloroform/10 methanol revealed a mixture containing five components. Three of these were isomers of XXIII with Rf's of 0.52, 0.52 and 0.55, and they accounted for 95% of the mixture. The two impurities had Rf's of 0.43 and 0.60.

E. N,N',N''-tri(2',3'-dihydroxypropyl) 3,5-bis-acetamido-2,4,6-triiodobenzamide (XXV)

The oxidation of XXIII was repeated twice with a sample of N,N',N''-triallyl 3,5-bis-acetamido-2,4,6-triiodobenzamide which had been crystallized and then further purified by silica gel column chromatography (40-140 mesh silica, toluene/acetone gradient) to yield a greater than 99% pure starting material. XXIII (2.70 g, 3.68 mMole) was added to a solution of acetone (30 ml) and water (3.4 ml) to yield a white slurry. t.-butyl hydroperoxide (2.85 ml of a 70% solution, 23.6 mMole) and osmium tetroxide (0.44 ml of a 0.0856M solution) were added next, which led to complete dissolution of the solids to yield a clear, pale yellow solution within an hour. The reaction was complete in less than 20 hours and gave a very complex mixture of products.

The crude material was isolated by pouring the reaction mixture into water and extracting the OsO4 and t.-butyl hydroperoxide with ethyl acetate (5×20 ml portions). The ethyl acetate extract was back-extracted with water (20 ml), the aqueous extracts were combined, and the water was removed to yield a clear, viscous liquid.

The crude product was analyzed by HPLC (25 cm×10 mm ID Alltech, NH2 10μcolumn, 90/10 acetonitrile/water, 10 ml/min). More than 20 components could be resolved. Four of these with retention times of 14.5, 19, 22 ln3 24 minutes accounted for 60% of the mixture and were present in the ratio of about 23:46:26:5. They were isolated individually and slowly interconverted at room temperature and somewhat faster in boiling water. These products are considered to be isomers of N,N',N",-tri-(2,3-dihydroxypropyl) 3,5-bis-acetamido-2,4, 6-triiodobenzamide (XXVI).

EXAMPLE VII

The following is the preparation of N,N',N'''-tri(2',3'-dihydroxypropyl) N"-acetyl 2,4,6-triiodoisophthaldiamide (Iohexol)

A. N,N'-diacetyl 5-(diacetimido)-2,4,6-triiodoisophthaldiamide (XXVII)

To a cooled, stirred suspension of 5-amino-2,4,6-triiodo isophthaldiamide (IX) (20 g, 0.036 mole) in acetic anhydride (120 ml), conc H2SO4 (7 ml) was added through an addition funnel in 20 min. The contents were stirred at approximately 50° C. for 7 hrs and the reaction allowed to continue overnight at room temperature. The reaction mixture was then poured into ice cold water (900 ml); the resulting white solid was filtered, washed successively with water (500 ml), 10% bicarbonate solution and water. It was then triturated with toluene, the solvent removed and the solid dried under vacuum at 44° C. As indicated by TLC, the product contained nearly 85% of tetracetyl (XXVII) and 15% of triacetyl (XXVIII). Yield: 21.75 g (~81%). For preparative purposes, this mixture was employed without further purification.

For analytical purposes, the tetraacetyl (XXVII) was separated from the triacetyl (XXVIII) by silica gel column chromatography using benzene-acetone as solvent. The tetraacetyl sintered at 265° and melted at 268°–70° C. with decomposition. For analysis, the compound was dissolved in acetone, filtered, and the solvent removed and dried.

| TLC | Rf: 0.56 in MeOH/CHCl3 (1:9) |
|---|---|
| | 0.69 in acetone/C6H6 (4:6) |

B. N,N'-diallyl 5-(N'''-acetyl, N'''-allyl amino)-2,4,6-triiodoisophthaldiamide (XXX)

To a stirred solution of crude tetraacetyl (XXVII) (2.69 g, 3.72 mMole) in dimethyl acetamide (13 ml), powdered potassium hydroxide (0.937 g, 16.73 mMole) was added and the contents stirred at 40° C. for approximately 4 hrs. TLC indicated that the product had 90% of (XXVIII), with diacetyl derivative and starting material as impurities.

To the above reaction mixture were added sodium bicarbonate (0.336 g, 4 mMole), potassium carbonate (0.75 g, 5.56 mMole) and then allyl chloride (1.8 ml, 22.2 mMole) and the contents stirred at ~40° C. overnight. The resulting triallyl triacetyl derivative (XXIX) was hydrolysed with 1N sodium hydroxide (9.5 ml) and water (5 ml) at 50° C. in 1.5 hr. The reaction mixture from which the product had partly precipitated out was poured into ice cold water, the solid filtered, washed and dried (yield: 1.82 g, ~70%). XXX crystallized from acetone-hexane as colorless needles; m.p.: 261°–262° (decomp).

| TLC | Rf: 0.63 in acetone/C6H6 (4:6) |
|---|---|
| | 0.43 in MeOH/CHCl3 (5:95) |

C. 1. N,N'-di(2',3'-dihydroxypropyl) 5-(N"-2",3"-dihydroxypropyl N"-acetyl amino)-2,4,6-triiodoisophthaldiamide (XXXI)

To a cooled, stirred suspension of (XXX) (2 g, 2.78 mMole) in acetone (10 ml) were added aqueous tetraethyl ammonium acetate (0.125 g, 0.55 mMole), 70% aqueous t.-butyl hydrogen peroxide (1.6 ml, 12.5 mMole), and aqueous osmium tetroxide (0.007 g, 0.028 mMole). The reaction mixture was kept in an oil bath for 3 hrs. at 45°–48° and the reaction allowed to continue at room temperature overnight. Excess peroxide was removed from the reaction mixture with 10% aqueous sodium sulphite solution (10 ml); after adjusting the pH to 6.5 with diluted HCl, the solution was evaporated to dryness *in vacuo*. The product was dissolved in water (30 ml), adsorbed in a column of diaion and the column eluted with water, water-methanol mixture. From water and methanol-water (10%) eluents, (XXXI) was obtained (1.80 gm, 85% yield) as a white powder.

Comparison of XXXI with an authentic sample of Iohexol (supplied by Nyegaard Co.) showed it to be identical in all respects.

| TLC | Rf: 0.42 in MeOH/CHCl3 (4:6) |
|---|---|
| | 0.49 faster moving isomer (90%) and |
| | 0.43 slower moving isomer (10%) in |
| | n-Butanol-water-acetic acid (50:25:11) |
| UV | (H2O) λmax 247.6 nm (εmax 27,900) |
| IR | KBr, υ max(cm$^{-1}$) 3200–2400 (OH stretch), |
| | 1610-1660 (>C = 0 stretch) |
| HPLC | Retention time 3.95 min (—NH2 column, |
| | 5 μm; E. Merck; CH3CN/H2O (85:15) |
| PNMR | (DMSO-d6), σppm) 1.8 (3H, S, —CO—CH3), |
| | 2.85-4.1 (15H, multiplets, CH2 and CH |
| | protons), 4.3–4.9 (6H, OH), 8.5 (2H, |
| | quartet, —CO—NH—). |
| Iodine content: theory: 46.36% Found: 46.2% |

C. 2. N,N'-di(2',3'-dihydroxypropyl) 5-(N"-2",3"-dihydroxypropyl N"-acetyl amino)-2,4,6-triiodoisophthaldiamide (XXXI) (Iohexol) (XXXI) (Alternate synthesis).

5-Acetamido-2,4,6-triodo-N,N'-bis-acetylisophthaldiamide (XXVIII) (50 mg, 0.073 mMoles) was added to a stirred suspension of sodium hydride (90%, 8.3 mg, 0.31 mMoles) in DMA (0.7 ml) at room temperature. After 30 min., 2,3-diacetoxypropyl chloride (70 μl, 0.43 mMoles) was added and the contents heated at 50°. Additional quantities of NaH (11 mg, 0.41 mMoles) and 2,3-diacetoxypropyl chloride (100 μl 0.61 mMoles) were added at intervals. After 6 days, the reaction mixture was hydrolyzed with 1N NaOH at 50°. The product was isolated by neutralizing the reaction mixture, removing the solvents and purifying on a diaion column euted with water, water-methanol mixture. Removal of the solvents gave a product in 87% yield which was identified as Iohexol (XXXI).

D. Isopropylidination of N,N'-di(2',3'-dihydroxypropyl) 5-(N''-(2''-3''-dihydroxypropyl) acetamido-2,4,6-triiodoisophthaldiamide (XXXI).

To a heterogeneous suspension of Iohexol (XXXI) (0.50 g, $6.1 \times 10^{-4}$ moles) in 3 ml 2,2-dimethoxy propane was added p-toluene sulfonic acid monohydrate (0.0024 g, $1.26 \times 10^{-5}$ moles), and the reaction mixture was warmed at 55° C. for 2.5 hrs. TLC (silica gel, 95/5 CHCl₃/MeOH) showed conversion to a single product.

Workup was accomplished by adding excess aqueous sodium bicarbonate to the reaction mixture, followed by pouring the reaction mixture into chloroform (50 ml). The layers were separated in a separatory funnel, and the aqueous layer was extracted with chloroform ($2\times15$ ml). The combined chloroform extracts were washed with 20% aqueous sodium bicarbonate (20 ml$\times$1), water ($2\times20$ ml) and 50% saturated brine (15 ml). The organic layer was dried over MgSO₄, the drying agent removed by filtration, and the solvent removed on a rotary evaporator. This gave 492 mg of N,N'-di(1',3'-dioxa-2',2'-dimethylcyclopentyl-3'-methyl) 5-(N''-1'',3'-dioxa-2',2''-dimethylcyclopentyl-3''-methyl)-2,4,6-triiodoisophthaldiamide (XXXII) as a white granular solid (86% yield). The product was dissolved in hot n-butanol and left to crystallize. Heating with a catalytic amount of Dowex 50, *in vacuo*, gave Iohexol, in high yield.

The following example illustrates the use of O-protected 2,3-dihydroxypropyl chloride for reaction with amides and imides for preparation of non-ionic contrast media.

EXAMPLE VIII

A. Synthesis of N-(2',3'-dihydroxypropyl) 3,5-(N',N''-2'',3''-dihydroxypropyl)acetamido-2,4,6-triiodobenzamide N,N',N''-triacetyl 3,5-diamino-2,4,6-triiodobenzamide (XXXIV) (76 mg; 0.12 mMoles) was added with stirring and cooling to a suspension of sodium hydride (17 mg; 0.7 mMoles) in dry DMA (1.2 ml). After 30 min., 2,3-diacetoxypropyl chloride (240 mg; 1.24 mMoles) and tetrabutylammonium bromide (33 mg; 0.1 mMoles) were added and the mixture was heated at 50° C. overnight.

TLC over silica gel using chloroform: ethanol (9:1) as eluent showed complete disappearance of the starting material (Rf 0.3) and the formation of two faster moving products whose Rf values (0.57 and 0.6) corresponded with the isomers of the expected product.

The reaction mixture was acidified with 1N HCl, extracted first with toluene ($3\times10$ ml) to remove non-polar colored impurities, and then with THF ($3\times10$ ml). The THF layers were combined, washed with brine ($2\times10$ ml) and dried (MgSO₄). Removal of the solvent, followed by preparative TLC over silica gel using chloroform: ethanol (9:1) as eluent, yielded the fully acetylated compound (XXXV).

Deacetylation of compound (XXXV) was achieved by treating a methanolic solution of (XXXIII) with a catalytic amount of sodium at room temperature. When the deacetylation was completed, as shown by TLC, the solution was treated with Dowex-50 (H+), to remove the sodium ion, and filtered. Removal of the solvent yielded the product N-(2',3'-dihydroxypropyl) 3,5-(N',N''-2'',3''-dihydroxypropyl)acetamido-2,4,6-triiodobenzamide.

In accordance with the subject invention, novel efficient techniques are provided for production of non-ionic contrast media based on polyhydroxylated polyiodo benzamides, where there are present at least three nitrogen atoms, which are substituted with polyhydroxyalkyl groups. The method employs functionalizing a plurality of nitrogen atoms, either simultaneously or stepwise with olefinic or polyacetoxyalkyl or dioxolanylalkyl groups from 2–4 carbon atoms substituents which are functionalized with a group which allows for a stable covalent bond, e.g., activated halide, such as allylic halide, acyl or beta-oxy alkyl halide, where aryl carboxyamides are acylated before substitution with the halide. At least two of the three nitrogen atoms present in the molecule will be functionalized with an olefinic group or hydroxylated substitute. The functionalization with olefinic groups can be achieved under mild conditions in high yield. Once all the olefinic groups have been introduced, they may be simultaneously oxidized to glycols, so that from four to six hydroxyl groups are simultaneously introduced into the molecule to provide the non-ionic contrast media in high yield. The same polyhydroxy compounds can also be generated by alkylating one or more N-acylcarboxamide functionalities in a molecule with polyacetoxyalkyl or dioxolanylalkyl halides, followed by the removal of the protective groups. Thus, the difficultly employable and frequently expensive polyhydroxylated amines can be substituted by the more readily available and inexpensive olefins, such as allyl halides, and acryloyl halides or beta-oxy halides. The subject process can be used for making commercially available non-ionic contrast media, such as Iohexol, as well as novel non-ionic contrast media having improved properties.

Although the foregoing invention has been described in some detail by way of illustration and example for purposes of clarity of understanding, it will be obvious that certain changes and modifications may be practiced within the scope of the appended claims.

What is claimed is:

1. A method for preparing a non-ionic contrast medium which comprises reacting a compound of the formula:

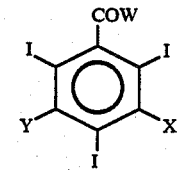

wherein:
W is amino, X is carboxamido and Y is amino with acryloyl chloride to form the acrylamide derivative;
acylating the nitrogens of the carboxamido groups with acetic anhydride;
allylating the acetylated carboxamido groups with allyl halide;
oxidizing the olefinic groups of said allyl groups and said acryloyl group to form a tris-glycol product.

2. A method according to claim 1, wherein the nitrogen of said Y group is mono-methylated prior to acetylation.

3. A method for preparing a non-ionic contrast medium which comprises reacting a compound of the formula:

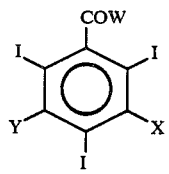

wherein:

W is chloro, X is chlorocarbonyl and Y is amino, with allylamine to form a diallyl substituted dicarboxamide;

reacting said diallyl substituted dicarboxamide with acryloyl chloride to form the acrylamide;

oxidizing the olefins of said allyl groups and said acryloyl group to form a tris-glycol.

4. A method according to claim 3, wherein said nitrogen of said Y group is methylated with a methyl halide.

5. A method according to claim 3, wherein polyhydroxyalkyl halides are substituted for said allyl halides, wherein said hydroxy groups are protected by ester or ether functionalities.

6. A method according to claim 5, wherein said polyhydroxyalkyl halides are polyacetoxyalkyl chlorides of from 3 to 4 carbon atoms and 2 to 3 acetoxy groups, respectively.

* * * * *